US012788999B2

(12) United States Patent
Alleman et al.

(10) Patent No.: US 12,788,999 B2
(45) Date of Patent: *Nov. 10, 2026

(54) IMPLANTABLE MEDICAL DEVICE AND ELECTRODE THEREOF

(71) Applicant: Pacesetter, Inc., Sylmar, CA (US)

(72) Inventors: Wesley Alleman, Santa Clarita, CA (US); Keith Victorine, Santa Clarita, CA (US); Tyler Strang, Santa Clarita, CA (US); Nicole Cooper, Burbank, CA (US); Steve Chantasirivisal, Santa Clarita, CA (US); Traci Chang, San Francisco, CA (US)

(73) Assignee: Pacesetter, Inc., Sylmar, CA (US)

( * ) Notice: Subject to any disclaimer, the term of this patent is extended or adjusted under 35 U.S.C. 154(b) by 95 days.

This patent is subject to a terminal disclaimer.

(21) Appl. No.: 18/976,925

(22) Filed: Dec. 11, 2024

(65) Prior Publication Data

US 2025/0099770 A1 Mar. 27, 2025

Related U.S. Application Data

(63) Continuation of application No. 17/372,854, filed on Jul. 12, 2021, now Pat. No. 12,201,846.

(51) Int. Cl.

| | |
|---|---|
| ***A61N 1/375*** | (2006.01) |
| ***A61N 1/05*** | (2006.01) |
| ***H01B 1/02*** | (2006.01) |
| ***H01B 7/04*** | (2006.01) |

(52) U.S. Cl.

CPC ........... *A61N 1/3752* (2013.01); *A61N 1/056* (2013.01); *H01B 1/02* (2013.01); *H01B 7/048* (2013.01)

(58) Field of Classification Search

CPC .... A61N 1/3752; A61N 1/056; A61N 1/0563; A61N 1/0565; A61N 1/362; A61N 1/39–1/3993; H01B 1/02; H01B 7/048; A61B 5/29; A61B 2562/227

See application file for complete search history.

(56) References Cited

U.S. PATENT DOCUMENTS

| | | | | |
|---|---|---|---|---|
| 4,280,511 | A | 7/1981 | O'Neill | |
| 6,253,110 | B1 * | 6/2001 | Brabec | A61N 1/0568 607/116 |
| 6,292,703 | B1 * | 9/2001 | Meier | A61B 5/287 607/118 |
| 7,184,839 | B2 | 2/2007 | Clemens et al. | |
| 8,017,179 | B2 | 9/2011 | Atanasoska et al. | |
| 8,364,281 | B2 | 1/2013 | Duncan et al. | |
| 9,682,229 | B2 | 6/2017 | Wu et al. | |

(Continued)

OTHER PUBLICATIONS

Medtronic Product Performance eSource, CapSure Sense Model 4574, dated Jun. 8, 2026 (2 pages).

(Continued)

*Primary Examiner* — Jonathan T Kuo

(74) *Attorney, Agent, or Firm* — Dean D. Small; Carroll, Hoette & Butscher, LLC

(57) ABSTRACT

An implantable medical device includes an electrode and an insulative material secured to the electrode. The electrode includes a metal substrate and a metal coating. The metal coating is disposed on an outer surface of the metal substrate. The insulative material is secured to the electrode via an adhesive that adheres to the metal coating.

20 Claims, 6 Drawing Sheets

(56) References Cited

U.S. PATENT DOCUMENTS

| | | | |
|---|---|---|---|
| 10,406,349 | B2 | 9/2019 | Shi et al. |
| 2007/0049985 | A1 | 3/2007 | Kessler et al. |
| 2010/0137928 | A1 | 6/2010 | Duncan et al. |
| 2014/0142670 | A1 | 5/2014 | Radhakrishnan et al. |
| 2014/0296955 | A1 | 10/2014 | Jang |

OTHER PUBLICATIONS

Boston Scientific Corporation, "Boston Scientific receives FDA approval for expanded indication of INGEVITY+ Pacing Leads to include system pacing of the left bundle branch area", Marlborough, Mass., Sep. 17, 2024 (3 pages).

"Boston Scientific Receives U.S. FDA Approval For Quadripolar Leads And Initiates Global Trial To Expand MRI Labeling To The U.S. And Asia", Marlborough, Mass., Feb. 23, 2016 (2 pages).

US Food & Drug Administration, "Class 1 Device Recall Reliance 4FRONT", dated Aug. 20, 2025 (4 pages).

Medtronic, Inc., "Capsure Sense 4073", Technical Manual, dated Oct. 13, 2013 (14 pages).

Medtronic, Inc., "Capsure Sense 4074", Technical Manual, dated May 6, 2017 (14 pages).

US Food & Drug Administration, "Acuity X4 Lead Models 4671, 4672, 4674, 4675, 4677, 4678", Boston Scientific Corp, dated Nov. 22, 2016 (2 pages).

US Food & Drug Administration, "Contak CD, Easytrak, Livian, Cognis, and Acuity Spirial Automatic Implantable Cardiac Resynchronization Therapy Defibrill", Boston Scientific Corp, dated Jun. 2, 2017 (2 pages).

US Food & Drug Administration, "Acuity X4 Straight (4671,4672), Spiral S (4674,4675), Spiral L, (4677,4678) Leads; Sutureless Sleeve & Flushing Tool/Wire", Boston Scientific Corp, dated Aug. 7, 2015 (8 pages) (2 pages).

Medtronic Inc., "Sprint Quattro Secure S MRI SureSCAN 6935M55, 6935M62", Technical Manual, dated Dec. 15, 2023 (18 pages).

Medtronic Inc., "Sprint Quattro Secure S 6935M49, 6935M72, 6935M97", Technical Manual, dated Dec. 15, 2023 (18 pages).

Medtronic Inc., "Sprint Quattro Secure S MRI SureScan™ 693558, 693565", Technical Manual, dated Dec. 15, 2023 (16 pages).

Medtronic Inc., Technical Manual, "Sprint Quattro Secure S 693552, 693575, 6935100", Technical Manual, dated Dec. 15, 2023 (16 pages).

Medtronic Inc., "CapSure Sense MRI SureScan 407452, 407458", Technical Manual, dated Nov. 20, 2023 (16 pages).

Medtronic Inc., "CapSure Sense MRI SureScan 457445, 457453", Technical Manual, dated Aug. 2, 2022 (16 pages).

Summary of Safety and Effectiveness Data, "Medtronic SelectSecure Lead Model 3830", Medtronic, PMA P030036B, dated Aug. 3, 2005 (22 pages).

Summary of Safety and Effectiveness Data, "Pulse Generator (PG): Implantable Pacemaker Lead: Steroid-eluting, endocardial, bipolar, pace/sense lead Lead stabilizer accessory Stylet accessories", Boston Scientific Corporation, PMA P150012, dated Apr. 25, 2016 (82 pages).

Summary of PMA P830061/S086, "Capsure Sense Lead, Medtronic" (13 pages).

US Food and Drug Administration, "Ingevity + Lead—Active Fixation", Boston Scientific, PMA 150012, dated Sep. 26, 2019 (3 pages).

US Food and Drug Administration, "Siello S 45, Siello S 53, Siello S 60, Solia S45, Solia S53, Solia S60", Biotronik Inc, PMA P950037, dated Jun. 1, 2015 (3 pages).

US Food and Drug Administration, "Sprint Quattro Secure S Single Coil IS-1/DF-1, Active Fix Lead Model 6935", Medtronic Inc, PMA P920015 dated Mar. 3, 2008 (3 pages).

US Food and Drug Administration, "Medtronic Sprint Quattro Secure Lead Model 6947M", Medtronic Inc, PMA P920015, dated Dec 4, 2009 (3 pages).

US Food and Drug Administration, "Medtronic Selectsecure Lead Model 3830", Medtronic, PMA P030036, dated Sep. 4, 2003 (16 pages).

US Food and Drug Administration, "Siello S45, Siello S 53, Siello S 60, Solia S45, Solia S 53, Solia S60", Biotronik Inc, PMA P950037, dated Jun. 1, 2015.

FDA report, "Sprint Quattro Model 6944 Lead PMA P920015S017", Medtronic, PMA P920015, dated Jun. 20, 2000 (2 pages).

Boston Scientific, "Evaluation of Acuity™ X4 Quadripolar Coronary Venous Leads and Reliance™ 4-FRONT Defibrillation Leads", Dec 17, 2013 (101 pages).

Biotronik website products page, "Solia S", Accessed Jul. 30, 2026, (10 pages).

* cited by examiner

IMPLANTABLE MEDICAL DEVICE AND ELECTRODE THEREOF

CROSS-REFERENCE TO RELATED APPLICATIONS

This application is a continuation of U.S. patent application Ser. No. 17/372,854, filed Jul. 12, 2021 and entitled Implantable Medical Device And Electrode Thereof, which is incorporated by reference herein in its entirety.

BACKGROUND

Embodiments of the present disclosure generally relate to implantable medical devices and methods, and more particularly to implantable medical devices having electrodes.

Implantable medical devices (IMDs) are utilized to monitor physiologic activity and deliver therapy to a patient, such as to the heart of the patient. IMDs can include, for example, pacemakers with leads, leadless pacemakers, neurostimulation devices, pressure sensors, and/or the like. The IMDs typically include one or more electrodes for sensing (e.g., monitoring) signals and/or delivering stimulation therapy. The electrodes are often bonded to electrically insulative materials that provide electrical insulation. For example, an electrode may be disposed on a lead of an IMD, and the electrode may be bonded to an insulative material of a lead body of the lead. The insulative material surrounds one or more conductors of the lead that convey electrical signals between a device body and the electrodes. The insulative material may be bonded to the electrode via the use of an adhesive. The electrodes in leadless IMDs also can be adhesively bonded to insulative materials.

When implanted in the patient, the adhesive bond between the insulative material and the electrode is typically exposed to a harsh environment both chemically and mechanically (e.g., physically). For example, a lead that is attached to the inner walls of a beating heart for a number of years can fatigue due to the normal body function cycling. Furthermore, movement of the patient in which the IMD is implanted can cause a lead to rub against bone, other leads, the device body, or the like, which can apply strain to the adhesive bonds. In addition, some electrodes are composed of inert metals that do not bond well to the adhesive.

A need remains for an IMD that includes strong adhesive bonds between an electrode and an insulative material, to improve reliability and enhance device safety and efficacy, throughout the operational life cycle of the IMD.

SUMMARY

In one or more embodiments, an implantable medical device is provided that includes an electrode and an insulative material secured to the electrode via an adhesive. The electrode includes a metal substrate and a metal coating. The metal substrate includes a connection segment and an active segment along a length of the metal substrate. The metal coating is disposed on an outer surface of the metal substrate along the connection segment and the active segment. The insulative material surrounds the connection segment of the metal substrate without surrounding the active segment, and the adhesive adheres to the metal coating on the connection segment.

Optionally, the metal substrate has a hollow generally cylindrical shape that defines a channel extending from a first end of the metal substrate to a second end of the metal substrate opposite the first end. The connection segment is a first connection segment that extends from the active segment to the first end. A second connection segment of the metal substrate extends from the active segment to the second end. Optionally, the metal substrate has an inner surface opposite the outer surface, and the inner surface defines the channel. The metal coating is disposed on the inner surface along at least the first connection segment.

Optionally, the connection segment is a first connection segment, and the active segment is disposed between the first connection segment and a second connection segment of the metal substrate along the length of the metal substrate. The metal coating is not disposed along the second connection segment.

Optionally, the metal substrate includes at least one of platinum, iridium, or titanium. Optionally, the metal coating includes one of titanium nitride, platinum black, or iridium oxide. For example, the metal substrate may include a platinum alloy, and the metal coating may include titanium nitride. Optionally, the outer surface of the metal substrate on which the metal coating is applied is generally smooth. Optionally, the insulative material comprises at least one of silicone or polyurethane. The insulative material may be a tube that surrounds one or more conductors.

Optionally, the connection segment of the metal substrate defines multiple apertures through a thickness of the metal substrate.

Optionally, the electrode is a ring electrode attached to a lead, and the implantable medical device further comprises a tip electrode separated from the ring electrode by a length of the lead.

In one or more embodiments, an electrode for an implantable medical device is provided. The electrode includes a metal substrate and a metal coating. The metal substrate has a connection segment and an active segment along a length of the metal substrate. The metal substrate is composed of at least one of platinum, iridium, or titanium, and the connection segment is configured to be bonded to an insulative material of the implantable medical device via an adhesive. The metal coating is disposed on an outer surface of the metal substrate along both the connection segment and the active segment. The metal coating is composed of one of titanium nitride, platinum black, or iridium oxide.

Optionally, the connection segment is a first connection segment, and the active segment is disposed between the first connection segment and a second connection segment of the metal substrate along the length of the metal substrate. The metal coating is not disposed along the second connection segment.

Optionally, the metal substrate defines a channel extending the length of the metal substrate. The channel is defined by an inner surface of the metal substrate opposite the outer surface. The metal coating is disposed on the inner surface along at least the connection segment.

Optionally, the metal substrate includes a platinum alloy, and the metal coating includes titanium nitride. Optionally, the outer surface of the metal substrate on which the metal coating is applied is generally smooth. Optionally, the connection segment of the metal substrate defines multiple apertures through a thickness of the metal substrate for anchoring the adhesive to the connection segment.

In one or more embodiments, a method of providing an electrode is disclosed. The method includes forming a metal substrate to include a connection segment and an active segment along a length of the metal substrate. The metal substrate is composed of at least one of platinum, iridium, or titanium. The connection segment is configured to be bonded to an insulative material of an implantable medical device via an adhesive. The method also includes applying a metal coating on an outer surface of the metal substrate along both the connection segment and the active segment. The metal coating is composed of titanium nitride, platinum black, or iridium oxide.

Optionally, the method also includes applying the adhesive on the metal coating along the connection segment for bonding to the insulative material.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Figure 1:
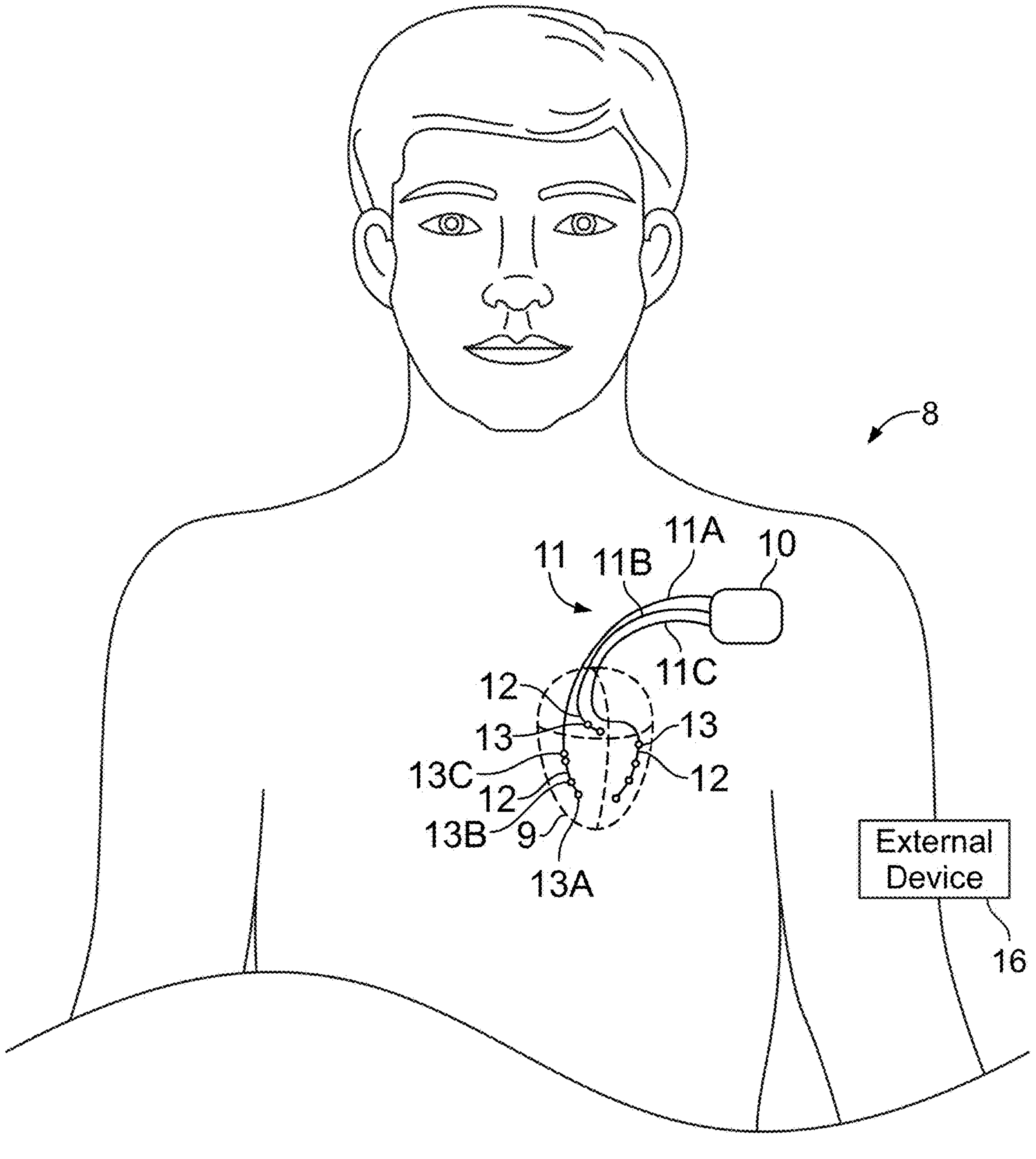
FIG. 1 illustrates an implantable medical device (IMD) coupled to a heart in a patient and implemented in accordance with one embodiment.

FIG. 1 illustrates an implantable medical device (IMD) 8 coupled to a heart 9 in a patient and implemented in accordance with one embodiment. The IMD 8 may be a cardiac pacemaker, an implantable cardiac monitoring device (ICM), a defibrillator, an ICM coupled with a pacemaker, or the like. The IMD 100 is intended for subcutaneous implantation at a site near the heart 9. The IMD 8 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. The IMD 8 may be controlled to sense atrial and ventricular waveforms of interest, discriminate between two or more ventricular waveforms of interest, deliver stimulation pulses for pacing and/or shocks, and inhibit application of a stimulation pulse to a heart based on the discrimination between the waveforms of interest and the like. Exemplary structure for the IMD 8 is discussed and illustrated below in connection with FIG. 9.

The IMD 8 includes a body or housing 10 that is connected to at least one lead 11. The leads 11 are cardiac leads that extend from the housing 10 to the heart 9 of the patient. A proximal end of each lead is connected to the housing 10, and a distal end of each lead is in contact with patient tissue surrounding the heart 9. Three leads 11 are shown in FIG. 1, but the IMD 8 may include more or less than three leads in another embodiment.

The leads 11 measure cardiac signals of the heart 9 and deliver stimulation therapy to the heart 9. For example, the leads 11 may detect intracardiac electrogram (IEGM) signals that form an electrical activity indicator of myocardial function over multiple cardiac cycles of the heart 9. The leads 11 may include a right ventricular lead 11A, a right atrial lead 11B, and a coronary sinus lead 11C. Each lead 11 includes a respective lead body 12 and at least one electrode 13. The leads 11 in the illustrated embodiment have multiple electrodes 13. The electrodes 13 may deliver electrical stimulation or pulses to the patient tissue in contact with the electrodes 13. The electrode 13 may also sense to receive cardiac signals (e.g., IEGM signals) from the heart 9. In an embodiment, a single electrode 13 may emit a stimulation pulse in a stimulation mode, and then may quickly switch to a monitoring mode to detect cardiac signals following the stimulation pulse.

The electrodes 13 may include a tip electrode 13A, a ring electrode 13B, a coil electrode 13C, and/or the like. On the right ventricular lead 11A, the tip electrode 13A is located at the distal end of the lead 11A, opposite the end extending from the housing 10. The ring electrode 13B and the coil electrode 13C of the lead 11A are disposed between the tip electrode 13A and the housing 10 along the length of the lead 11A, although are closer to the tip electrode 13A than to the housing 10. The tip electrode 13A is separated from the ring electrode 13B by a length of the lead body 12. The ring electrode 13B is separated from the coil electrode 13C by another length of the lead body 12.

The housing 10 may contain a battery, pulse generation circuitry, communication circuitry, a data storage device (e.g., memory), and/or control circuitry. The control circuitry is for receiving and analyzing electrocardiogram IEGM signals from the electrodes 13. The control circuitry may include at least one processor for processing the IEGM signals in accordance with algorithms to make determinations about the state of the heart 9. The memory provides storage for the cardiac signals and programmed instructions for the control circuitry. The battery powers the circuitry with the housing 10. For example, the battery powers the pulse generation circuitry to generate stimulation pulses and powers the communication circuitry to communicate with an external device 16. The control circuitry may generate messages to be communicated via the communication circuitry to the external device 16. The messages may include the IEGM signals and/or data generated based on the IEGM signals.

The external device 16 may represent a portable smartphone, tablet device, bedside monitor installed in a patient's home, or the like. The external device 16 may be a programmer device used in the clinic to interrogate the IMD 8, retrieve data and program detection criteria and other features. The external device 16 facilitates access by physicians to patient data as well as permits the physician to review real-time electrocardiogram (ECG) signals while being collected by the IMD 8.

Although several embodiments described herein are directed to IMDs with leads, one or more of the embodiments can be applied to leadless IMDs, such as a leadless pacemaker, neurostimulation device, pressure sensor, or the like. For example, the electrodes described herein optionally may be attached to a housing or case, instead of to a lead. The electrodes may be adhesively bonded to an insulative material of the housing or case, rather than an insulative material of a lead body of a lead.

Figure 2:
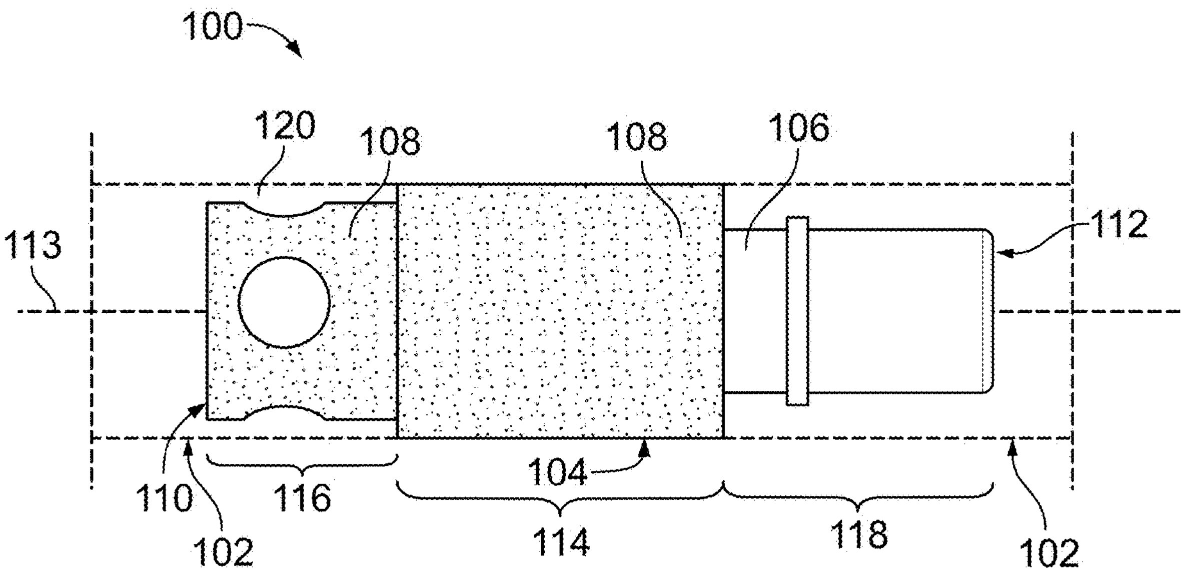
FIG. 2 is a side view of a portion of a lead of an IMD according to an embodiment.

FIG. 2 is a side view of a portion of a lead 100 of an IMD according to an embodiment. The lead 100 may be one of the leads 11 shown in FIG. 1. The lead 100 includes a lead body 102 and at least one electrode 104. In FIG. 2, the lead body 102 is shown in phantom, and one electrode 104 is depicted. The electrode 104 in FIG. 2 in an embodiment is a ring electrode, such as the ring electrode 13B shown in FIG. 1. The electrode 104 may be a different type of electrode in an alternative embodiment, such as a tip electrode.

The electrode 104 includes a metal substrate 106 and a metal coating 108 disposed on a portion of the metal substrate 106. The metal substrate 106 has a first end 110 and a second end 112. In the illustrated embodiment, the metal substrate is oriented about a length axis 113 from the first end 110 to the second end 112, such that the first end 110 is opposite the second end 112.

The metal substrate 106 includes an active segment 114 and at least one connection segment along the length of the metal substrate 106. The active segment 114 delivers stimulation pulses and/or senses cardiac signals. The metal coating 108 is located along the active segment 114. The metal coating 108 may enhance the electrical activity of the electrode 104 by increasing the surface area along an exposed outer surface of the electrode 104 at the active segment 114 and decreasing electrical polarization. Decreasing the electrical polarization reduces the amount of time that residual voltage remains on the electrode 104, which enables the electrode 104 to quickly switch from a stimulation mode to a sensing mode.

The connection segment(s) attach to the lead body 102 to secure the electrode 104 to the lead body 102. In the illustrated embodiment, the metal substrate 106 includes a first connection segment 116 and a second connection segment 118. The active segment 114 is disposed between the first and second connection segments 116, 118 along the length of the metal substrate 106. For example, the first connection segment 116 extends from the active segment 114 to the first end 110, and the second connection segment 118 extends from the active segment 114 to the second end 112.

The first connection segment 116 is secured to an insulative material 120 of the lead body 102 via an adhesive. The insulative material 120 refers to an electrically insulative material, such as a dielectric material. The insulative material 120 surrounds the first connection segment 116 of the metal substrate 106. The insulative material 120 does not surround the active segment 114. The insulative material 120 may be a tube or sleeve.

In one or more embodiments, the metal coating 108 is disposed on the first connection segment 116 in addition to the active segment 114. For example, the adhesive adheres to the metal coating 108 on the first connection segment 116. As described in more detail herein, the metal coating 108 increases the bond strength at the interface between the first connection segment 116 of the metal substrate 106 and the insulative material 120 of the lead body 102, relative to not applying the metal coating 108 on the first connection segment 116.

The metal coating 108 on the active segment 114 is exposed to the external environment surrounding the lead 100. When implanted, the external environment includes organic endocardial tissues and fluids of the patient surrounding the lead 100. The metal coating 108 on the active segment 114 experiences physical contact with the patient tissues to establish direct and persistent electrode-tissue contact for efficient stimulation and accurate sensing. The metal coating 108 on the first connection segment 116 is covered by the insulative material 120 of the lead body 102. As such, the metal coating 108 on the first connection segment 116 does not physically contact the patient tissue.

In the illustrated embodiment, the metal coating 108 is not present on the second connection segment 118 of the metal substrate 106. The outer surface of the metal substrate 106 is covered with the metal coating 108 along the first connection segment 116 and the active segment 114, but not the second connection segment 118. The second connection segment 118 may be attached to a second portion of the lead body 102 via a different attachment mechanism than the first connection segment 116. For example, the second connection segment 118 may be connected to the lead body 102, or one or more conductors thereof, via welding.

In a first alternative embodiment, the second connection segment 118 is also coated with the metal coating 108. The outer surface of the metal substrate 106 may be coated with the metal coating 108 along the entire length of the metal substrate 106. This embodiment may be used when the second connection segment 118 is bonded to an insulative material of the lead body 102 via an adhesive, like the first connection segment 116.

In a second alternative embodiment, the metal substrate 106 of the electrode 104 does not include the second connection segment 118. For example, the metal substrate 106 may include only the connection segment 116 and the active segment 114 along the length of the metal substrate 106. Both the connection segment 116 and the active segment 114 are coated with the metal coating 108, as described above. This embodiment may be used when the electrode 104 is located at the distal end of the lead 100, such as a tip electrode.

Figure 3:
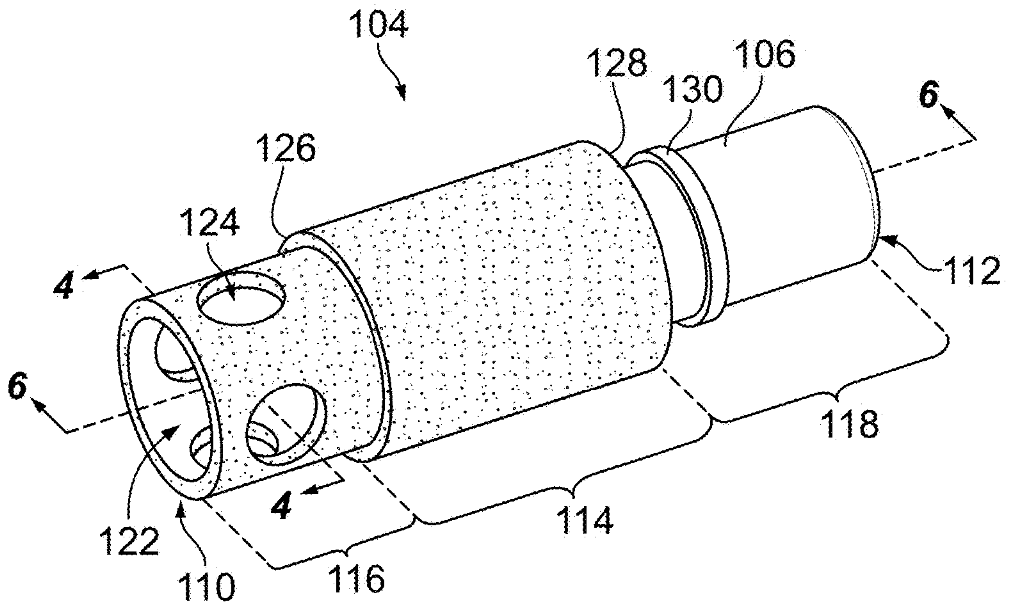
FIG. 3 is an isolated perspective view of an electrode of the lead shown in FIG. 2.

FIG. 3 is an isolated perspective view of the electrode 104 of the lead 100 shown in FIG. 2. The metal substrate 106 in the illustrated embodiment has a hollow, generally cylindrical shape that defines a channel 122 therethrough. The channel 122 extends from the first end 110 to the second end 112, and is open along both ends 110, 112. The channel 122 extends along the length axis 113 shown in FIG. 2. The metal substrate 106 may be formed via a molding or casting process. The metal substrate 106 may have a unitary, monolithic (e.g., one-piece) body such that the segments 114, 116, 118 are integrally connected at seamless interfaces. The active segment 114 may have a larger outer diameter than the connection segments 116, 118. For example, the first connection segment 116 may interface with the active segment 114 at a first stepped edge 126, and the second connection 118 may interface with the active segment 114 at a second stepped edge 128.

Figure 7:
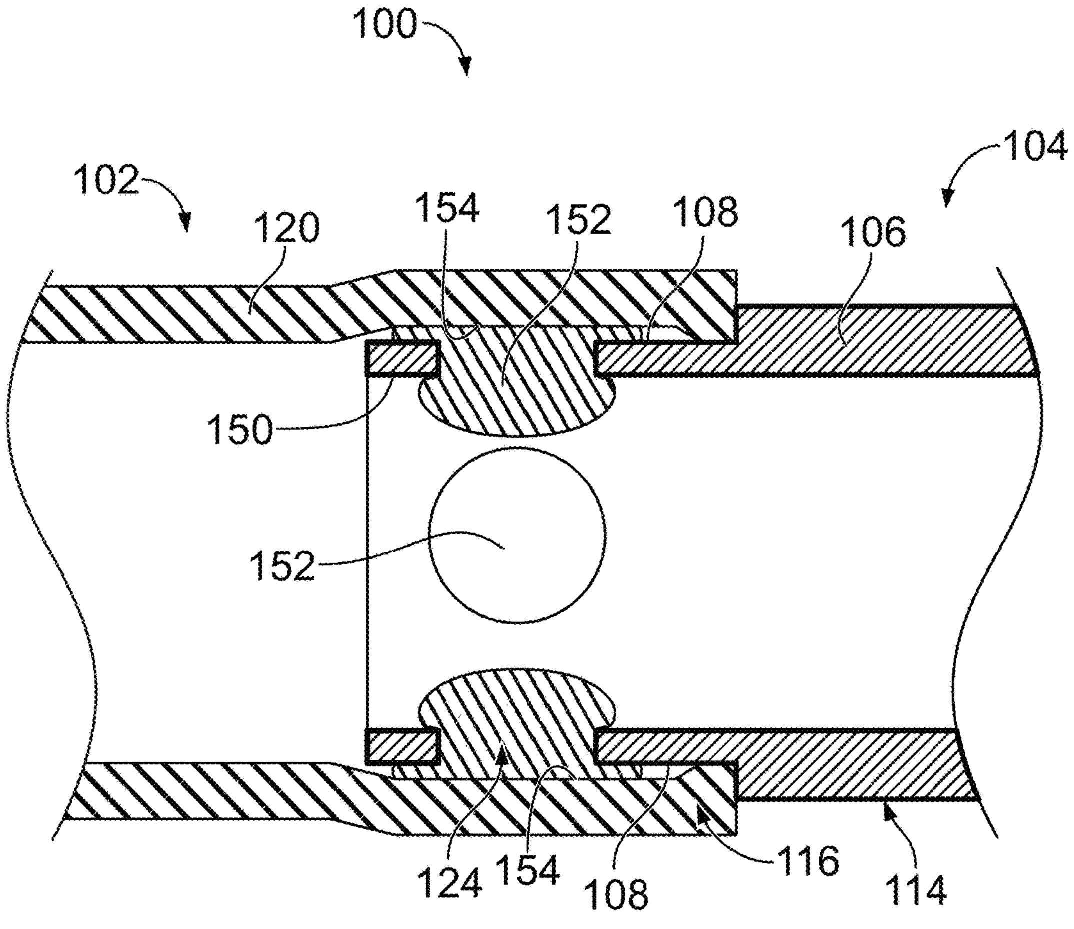
FIG. 7 is a close-up view of a portion of the cross-sectioned electrode shown in FIG. 6 with the first connection segment bonded to insulative material of the lead body according to an embodiment.

The first connection segment 116 may define one or more apertures 124 through a thickness of the metal substrate 106. When bonding the electrode 104 to the insulative material 120 of the lead body 102 (shown in FIG. 2) during lead assembly, the one or more apertures 124 provide contour for mechanically anchoring the adhesive to the electrode 104, as shown in FIG. 7. The first connection segment 116 includes four apertures 124 in the illustrated embodiment, but other embodiments may include more or less than four apertures 124. The apertures 124 are spaced apart along a circumference of the connection segment 116.

Optionally, the second connection segment 118 includes a flange 130 that extends circumferentially along the outer surface of the metal substrate 106. The flange 130 may be used to secure the second connection segment 118 to the lead body 102.

Figure 4:
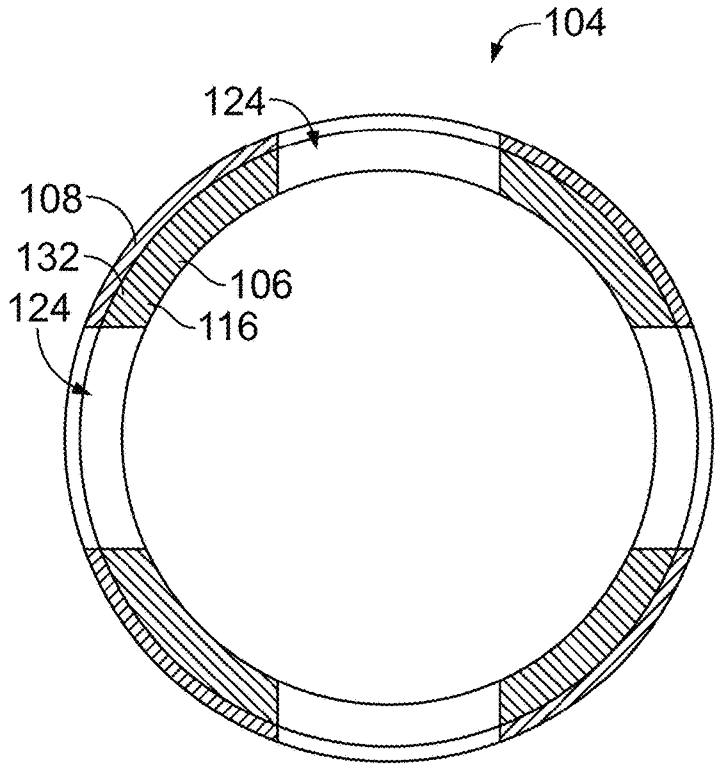
FIG. 4 is a cross-sectional view of the electrode taken along line 4-4 in FIG. 3.

FIG. 4 is a cross-sectional view of the electrode 104 taken along line 4-4 in FIG. 3. The illustrated view shows the first connection segment 118 of the metal substrate 106 and the metal coating 108. The cross-section extends across the apertures 124. The metal coating 108 is directly disposed on an outer surface 132 of the metal substrate 106. The metal coating 108 may be a thin layer that coats the outer surface 132. For example, the metal coating 108 may be thinner than the metal substrate 106 at the connection segment 116. The thickness of the metal coating 108 may be on the order of micrometers, such as between 1 and 1000 micrometers.

In one or more embodiments, the metal substrate 106 is composed of platinum, iridium, and/or titanium. These metals have beneficial properties for implantable electrodes. For example, these metals are inert and have relatively high corrosion resistance. For example, the metal substrate 106 may be a platinum alloy that includes platinum and at least one other metal. In a non-limiting example, the metal substrate 106 is a platinum iridium (Pt/Ir) alloy. In another example, the metal substrate 106 may be at least 90% platinum by weight of the metal substrate, such as at least 95% platinum by weight. Alternatively, the metal substrate 106 may be at least 90% by weight of titanium or iridium.

The downside of these metals is that it is difficult to form adhesive bonds between these metals and insulative materials due to the metals having generally poor bond strengths. For example, the adhesive does not strongly bond to the metal. The deposition of the metal coating 108 on the metal substrate 106, according to the embodiments described herein, remedies this issue by increasing the adhesive bond strength between the electrode 104 and the insulative material 120.

The metal coating 108 is composed of titanium nitride (TiN), platinum black, or iridium oxide. In at least one embodiment, the metal coating is TIN. In a non-limiting example, the metal coating is composed of TIN, and the metal substrate is composed of the Pt/Ir alloy or another platinum alloy. The TiN has a complex geometry with a fractal nature. The fractal nature of the TiN promotes the bonding between the metal substrate 106 and the adhesive used to secure the lead body insulative material 120. The platinum black and iridium oxide also have complex geometries that promote bonding between the metal substrate 106 and the adhesive by increasing the surface area of the electrode 104.

In the illustrated embodiment, the outer surface 132 of the metal substrate 106 is generally smooth. The metal substrate 106 is not subjected to an abrasive surface treatment to roughen the outer surface 132 prior to applying the metal coating 108 on the outer surface 132. For example, the metal substrate 106 is not subjected to grit blasting, sand blasting, or the like. Abrasive surface treatments on the inert metal surface of the electrode is one traditional technique for increasing the surface area of the metal improve adhesion between the electrode and the lead body, relative to applying the adhesive directly on a smooth surface of the electrode. In an embodiment, depositing the metal coating 108 on the first connection segment 116 of the electrode 104 provides yield sufficient bond strength to eliminate the need for the abrasive surface treatment. For example, the adhesive bond strength provided by applying an adhesive on the metal coating 108 disposed directly on a generally smooth outer surface 132 of the metal substrate 106 may be greater than the adhesive bond strength provided by applying the same adhesive directly on an abrasive surface-treated outer surface of the metal substrate. The electrode 104 according one or more embodiments does not utilize an abrasive surface treatment, which can reduce costs and increase throughput during the manufacturing process.

Figure 5:
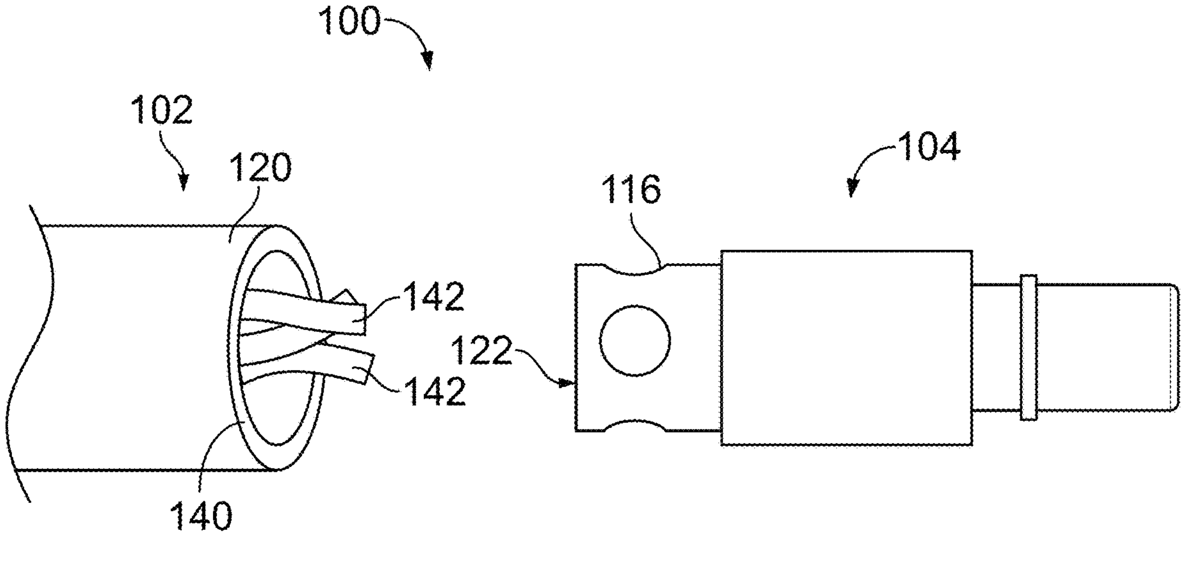
FIG. 5 illustrates an exploded view of the lead showing a lead body poised for attachment to a first connection segment of the electrode according to an embodiment.

FIG. 5 illustrates an exploded view of the lead 100 showing the lead body 102 poised for attachment to the first connection segment 116 of the electrode 104 according to an embodiment. In the illustrated embodiment, the insulative material 120 of the lead body 102 is a tube 140 that surrounds one or more conductors 142 of the lead 100. The conductors 142 may be metal wires or elements that provide an electrically conductive pathway for signal and/or stimulation transmission. The insulative material 120 (e.g., tube 140) is composed of one or more polymers. For example, the insulative material 120 may include silicone (e.g., silicone rubber), polyurethane, or a mixture of both. In a non-limiting example, the insulative material 120 is a silicone-polyurethane copolymer trademarked as Optim™. During assembly of the lead 100, the conductors 142 may extend into the channel 122 of the electrode 104, and the tube 140 is loaded onto the first connection segment 116 to surround the first connection segment 116.

Figure 6:
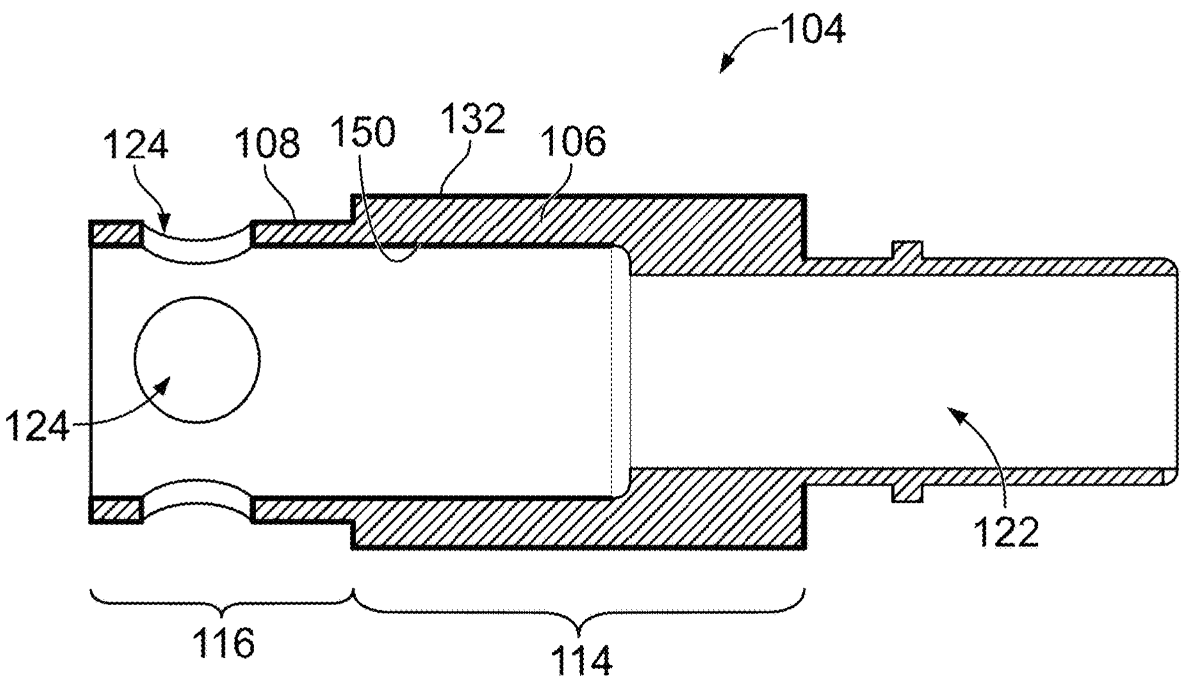
FIG. 6 is a cross-sectional view of the electrode taken along line 6-6 in FIG. 3.

FIG. 6 is a cross-sectional view of the electrode 104 taken along line 6-6 in FIG. 3. The metal substrate 106 has an inner surface 150 opposite the outer surface 132. The inner surface 150 defines the channel 122 through the metal substrate 106. Optionally, the metal coating 108 is disposed on both the outer surface 132 and the inner surface 150, along at least portion of the length of the metal substrate 106. For example, the metal coating 108 may be applied on the inner surface 150 along at least the first connection segment 116. Applying the metal coating 108 along the inner surface 150 of the first connection segment 116 may enhance the bonding of the adhesive to the metal substrate 106, particularly the portions of the adhesive that flow through the apertures 124. In one embodiment, the metal coating 108 is applied to the inner surface 150 along just the first connection segment 116 to conserve the metal coating material. In a second embodiment, the metal coating 108 is applied to the inner surface 150 along both the first connection segment 116 and the active segment 114. In a third embodiment, the metal coating 108 may be applied along the entire inner surface 150 to avoid masking the inner surface 150.

FIG. 7 is a close-up view of a portion of the cross-sectioned electrode 104 shown in FIG. 6 with the first connection segment 116 bonded to the insulative material 120 of the lead body 102 according to an embodiment. To assemble the lead 100, after the metal coating 108 is applied on the first connection segment 116 the adhesive 152 is deposited on the metal coating 108 and/or on an interior surface 154 of the insulative material 120. The adhesive 152 may be a medical grade adhesive that is safe for use within a patient body. The adhesive 152 may be a silicone room temperature vulcanizing (RTV) sealant or the like. The insulative material 120 is then loaded onto the electrode 104 to surround the first connection segment 116 without surrounding the active segment 114.

The adhesive 152 is disposed between the metal coating 108 on the first connection segment 116 and the interior surface 154 of the insulative material 120. Portions of the adhesive 152 may flow into the apertures 124 and engage the inner surface 150 of the first connection segment 116. As the adhesive 152 solidifies, those portions within the apertures 124 may mechanically anchor the adhesive 152 in place relative to the electrode 104. The adhesive 152 bonds directly to the metal coating 108, instead of to the metal substrate 106 underneath the coating 108. The metal coating 108 provides greater bond strength than if the adhesive 152 is bonded to the metal substrate 106, particularly when the metal substrate 106 is composed of platinum, iridium, and/or titanium. Applying the metal coating 108 along the inner surface 150 of the first connection segment 116 may enhance the anchoring of the adhesive 152 to the electrode 104, relative to the inner surface 150 being uncoated.

The adhesive 152 may bond well to the insulative material 120 of the lead body 102, providing a strong connection between the electrode 104 and the lead body 102 that can withstand the harsh environment within the patient body, including prolonged exposure to organic fluids and impacts and abrasive forces due to patient body movement. The adhesive 152 also provides a hermetic seal at the interface between the electrode 104 and the lead body 102.

The metal coating 108 disclosed herein has favorable electrical properties and is applied on the surface of the active segment 114 of the electrode 104 to enhance polarization (e.g., quickly dissipate electric current from the electrode). The embodiments disclosed herein extend the coverage of the metal coating 108 to another segment of the electrode 104 and utilize the metal coating 108 for a different purpose. As described herein, the metal coating 108 is applied on the surface of the (first) connection segment 116. The complex geometry of the metal coating 108 provides increased surface area (e.g., "grip") to which an adhesive can adhere.

Applying the metal coating 108 on the connection segment 116 increases the adhesive bond strength between the electrode 104 and the insulative material 120 of the lead body 102, relative to depositing the adhesive directly on an untreated surface of the metal substrate 106. Furthermore, extending the metal coating 108 to the connection segment 116 to improve the bond strength can replace other techniques for improving the bond strength, such as performing abrasive surface treatments on the metal substrate 106. The application of the metal coating 108 to the connection segment 116 may not represent an additional manufacturing step, but rather merely an extension of a pre-existing step to apply a metal coating on the active segment 114 for the favorable electrical properties.

Extending the coverage of the metal coating 108 to include both the active segment 114 and the connection segment 116 may actually improve efficiency by reducing the amount of surface area that is masked prior to depositing the metal coating 108 on the metal substrate 106. For example, neither the active segment 114 nor the connection segment 116 gets masked before the metal coating 108 is applied. The masking process tends to be manual and laborious, so reducing the amount of masking can reduce costs and improve manufacturing efficiency and throughput.

Figure 8:
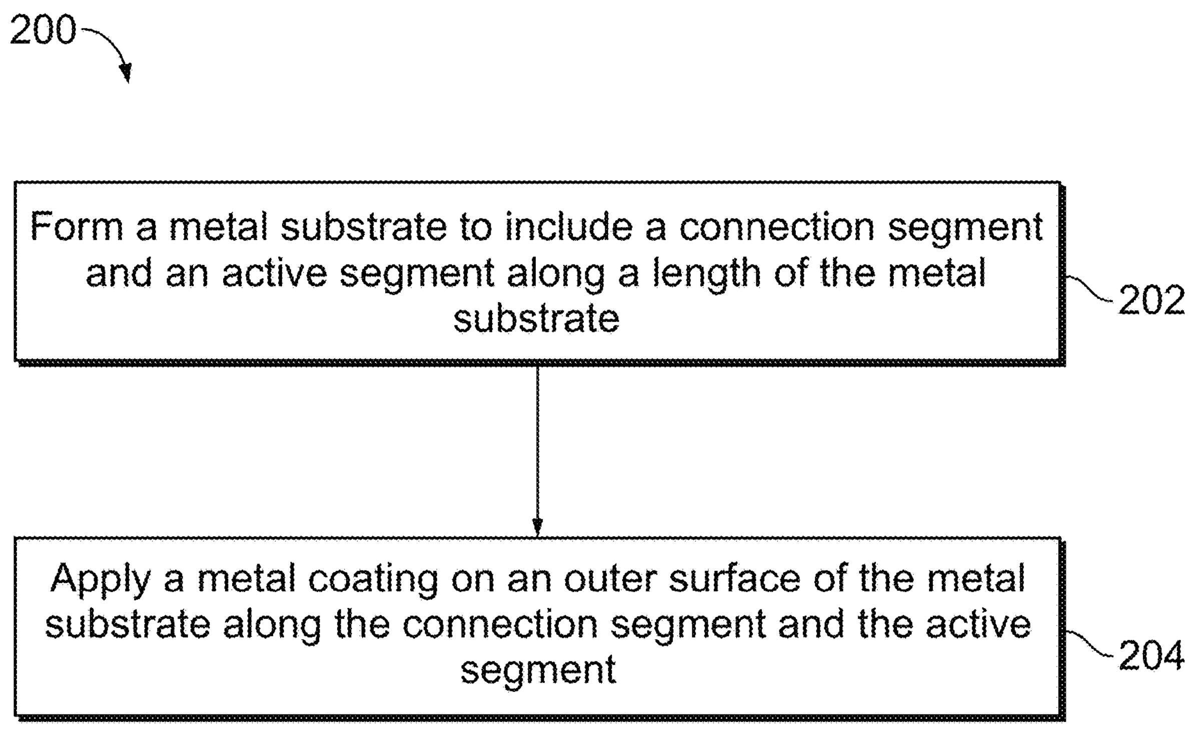
FIG. 8 is a flow chart of a method for providing an electrode for a lead of an IMD according to an embodiment.

FIG. 8 is a flow chart 200 of a method of providing an electrode of a lead for an implantable medical device (IMD) according to an embodiment. The method may be performed to produce the electrode 104 described with reference to FIGS. 2 through 7. The method may include more steps than shown in FIG. 8 and/or different steps than the steps shown in FIG. 8.

At 202, a metal substrate is formed to include a connection segment and an active segment along a length of the metal substrate. The metal substrate is composed of platinum, iridium, and/or titanium. The connection segment is configured to be bonded to an insulative material of a lead body via an adhesive. Optionally, the connection segment is formed to define multiple apertures through a thickness of the metal substrate for anchoring the adhesive to the connection segment. Optionally, the metal substrate is formed to also include a second connection segment. The metal substrate may be a ring electrode than has a generally cylindrical hollow shape.

At 204, a metal coating is applied on an outer surface of the metal substrate along the connection segment and the active segment. The metal coating is composed of titanium nitride, platinum black, or iridium oxide. The metal coating may be applied through any conventional coating technique, such as thermal spraying, electroplating, dipping, painting, cladding, vapor deposition, or the like. Optionally, the metal coating is also applied on an inner surface of the metal substrate along at least the connection segment. The inner surface defines a channel through the length of the electrode. Optionally, the metal coating is just applied to the connection segment and the active segment. The metal coating may not be disposed on other portions of the metal substrate, such as the second connection segment. Optionally, when the connection segment defines the apertures therethrough for anchoring the adhesive, the metal coating is also applied to the area of the metal substrate in and surrounding the apertures.

Optionally, the metal coating is applied to the outer surface after the metal substrate is formed without any intervening surface treatments, such as abrasive grit blasting, on the connection segment of the metal substrate. The outer surface of the metal substrate on which the metal coating is applied may be generally smooth.

The electrode produced via the method in FIG. 8 can be assembled with a lead body to form a lead, such as the lead 100 in FIG. 2. The assembly process optionally includes applying an adhesive on the metal coating along the connection segment for bonding to the insulative material of the lead body. The adhesive is a medical grade adhesive. After the adhesive is applied on the metal coating, the insulative material of the lead body, such as a tube, may be loaded onto the metal substrate to surround the connection segment. The adhesive may be sandwiched between the outer surface of the connection segment and the interior surface of the insulative tube. The adhesive bonds the insulative tube of the lead body to the electrode with sufficient bond strength to withstand the harsh conditions inside the patient body for a prolonged period of time without the adhesive interface failing.

Figure 9:
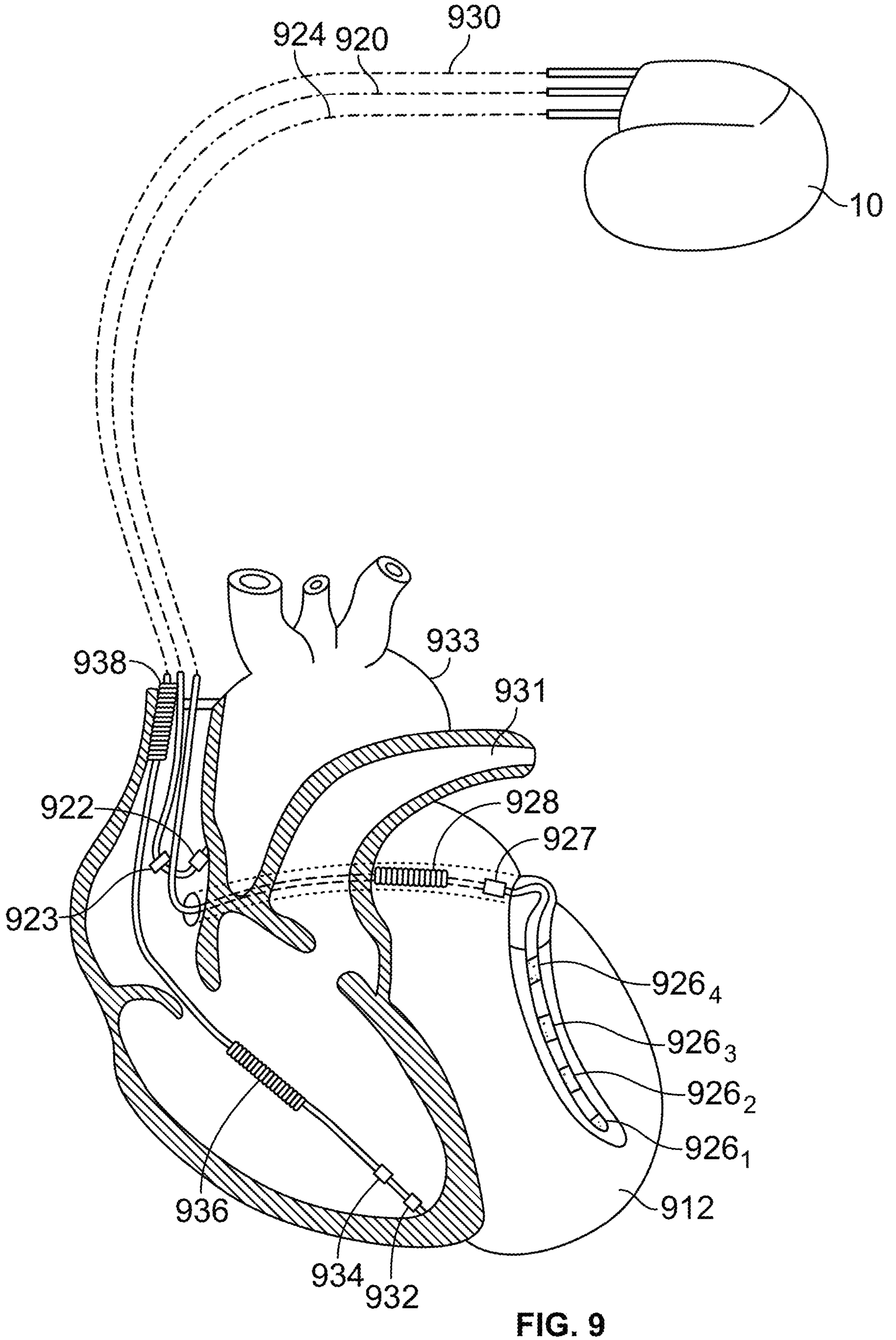
FIG. 9 illustrates a multi-lead IMD implanted proximate to a patient heart according to an embodiment.

FIG. 9 illustrates a multi-lead IMD 900 implanted proximate to a patient heart 912 according to an embodiment. The IMD 900 may be a dual-chamber stimulation device capable of treating both fast and slow arrhythmias with stimulation therapy, including cardioversion, defibrillation, and pacing stimulation. To provide other atrial chamber pacing stimulation and sensing, housing 901 is shown in electrical communication with the heart 912 by way of a left atrial lead 920 having an atrial tip electrode 922 and an atrial ring electrode 923 implanted in the atrial appendage. The housing 901 is also in electrical communication with the heart by way of a right ventricular lead 930 having, in this embodiment, a ventricular tip electrode 932, a right ventricular ring electrode 934, a right ventricular (RV) coil electrode 936, and a superior vena cava (SVC) coil electrode 938. Typically, the right ventricular lead 930 is transvenously inserted into the heart so as to place the RV coil electrode 936 in the right ventricular apex, and the SVC coil electrode 938 in the superior vena cava. Accordingly, the right ventricular lead 930 is capable of receiving cardiac signals, and delivering stimulation in the form of pacing and shock therapy to the right ventricle.

To sense left atrial and ventricular cardiac signals and to provide left chamber pacing therapy, the housing 901 is coupled to a multi-pole LV lead 924 designed for placement in the coronary sinus (CS) region, which refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 924 is designed to receive atrial and ventricular cardiac signals and to deliver left ventricular pacing therapy using a set of four left ventricular electrodes $\mathbf{926}_1$ (D1), $\mathbf{926}_2$ (M2), $\mathbf{926}_3$ (M3), and $\mathbf{926}_4$ (P4), (thereby providing a quad-pole lead), left atrial pacing therapy using at least a left atrial ring electrode 927, and shocking therapy using at least a left atrial coil electrode 928. The $\mathbf{926}_1$ LV electrode may also be referred to as a "tip" or "distal" LV electrode. The $\mathbf{926}_4$ LV electrode may also be referred to as a "proximal" LV electrode. In other examples, more or fewer LV electrodes are provided. Although only three leads are shown in FIG. 9, it should also be understood that additional leads (with one or more pacing, sensing and/or shocking electrodes) might be used and/or additional electrodes might be provided on the leads already shown, such as additional electrodes on the RV lead. Also, note that the P4 electrode $\mathbf{926}_4$ is preferably located in or near the AV groove, as discussed and described above. The details of this configuration are not necessarily shown in this particular figure.

It is noted that, in practice, electrodes 926 are on the "left heart lead" and depending upon where the lead is implanted, in most patients, all four electrodes can be in LV but in a substantial minority of patients the P4 electrode is situated in the LA (specifically in AV groove). As noted above, the P4 electrode is the electrode on which LA activation is sensed (which can also be present even if the electrode is primarily on the LV instead of LA). On present commercially-available hardware, there is often no separate electrode 927. That is, the P4 electrode $\mathbf{926}_4$ and the "left atrial ring electrode" 927 are one and the same. Hence, it should be understood that the "left atrial ring electrode" could instead be used as the P4 electrode, assuming it is suitably positioned in or near the AV groove. Both electrodes are shown for the sake of completeness and generality.

The embodiments described above with reference to FIGS. 2 through 8 may be applied to one or more of the electrodes and leads shown in FIG. 9.

While the foregoing embodiments are described in connection with an electrode on a lead, it is recognized that embodiments may be implemented with a variety of other implantable medical systems.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. For example, the electrode 104 in FIGS. 2 through 7 may be attached via an adhesive bond to a housing or header of the LIMD according to at least one of these patents and applications.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. For example, the electrode 104 in FIGS. 2 through 7 may be a component of a lead as described in at least one of these patents and applications. Further, one or more combinations of IMDs may be utilized from the above incorporated patents and applications in accordance with embodiments herein.

Additionally or alternatively, the IMD according to one or more embodiments may be a leadless cardiac monitor (ICM) that includes one or more structural and/or functional aspects of the device(s) described in U.S. Pat. No. 9,949,660, filed Mar. 29, 2016, entitled, "Method And System To Discriminate Rhythm Patterns In Cardiac Activity," which is expressly incorporated herein by reference. For example, the electrode 104 in FIGS. 2 through 7 may be attached via an adhesive bond to a housing or header of the ICM according to this patent.

Embodiments may be implemented utilizing all or portions of the methods and systems described in U.S. application Ser. No. 16/930,791, filed Jul. 16, 2020 and titled "Methods, Devices And Systems For Holistic Integrated Healthcare Patient Management".

Embodiments may be implemented in connection with one or more PIMDs. Non-limiting examples of PIMDs may include passive wireless sensors used by themselves, or incorporated into or used in conjunction with other IMDs such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties. For example, the electrode 104 in FIGS. 2 through 7 may be attached via an adhesive bond to a housing or header of the ICM according to at least one of these patents.

The physiologic sensor may be implemented as an accelerometer and may be implemented utilizing all or portions of the structural and/or functional aspects of the methods and systems described in U.S. Pat. No. 6,937,900, titled "AC/DC Multi-Axis Accelerometer for Determining A Patient Activity and Body Position;" U.S. application Ser. No. 17/192,961, filed Mar. 5, 2021, titled "System For Verifying A Pathologic Episode Using An Accelerometer"; U.S. application Ser. No. 16/869,733, filed May 8, 2020, titled "Method And Device For Detecting Respiration Anomaly From Low Frequency Component Of Electrical Cardiac Activity Signals;" U.S. application Ser. No. 17/194,354, filed Mar. 8, 2021, titled "Method And Systems For Heart Condition Detection Using An Accelerometer," the complete subject matter which is expressly incorporated herein by reference.

All references, including publications, patent applications and patents, cited herein are hereby incorporated by reference to the same extent as if each reference were individually and specifically indicated to be incorporated by reference and were set forth in its entirety herein.

It should be clearly understood that the various arrangements and processes broadly described and illustrated with respect to the figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the preceding description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The preceding description is intended only by way of example, and simply illustrates certain example embodiments.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Approximating language, as used herein throughout the specification and claims, may be applied to modify any representation that could permissibly vary without resulting in a change in the basic function to which it may be related. Accordingly, a term modified by "about," "substantially," "generally," and "approximately," is inclusive of conditions that permissibly vary from the stated term without resulting in a change of the basic function of the term. For example, the phrase "generally smooth" when used in reference to a surface can indicate that the surface appears smooth to the naked eye of an observer, although it is permissible and even probable that the surface under closer examination may include some imperfections and/or variations.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device comprising:

an electrode comprising a metal substrate and a metal coating, the metal coating disposed on an outer surface of the metal substrate; and an insulative material secured to the electrode via an adhesive that adheres to the metal coating.

2. The implantable medical device of claim 1, wherein the metal substrate comprises a connection segment and an active segment along a length of the metal substrate, wherein the metal coating is disposed on the outer surface of the metal substrate along both the connection segment and the active segment.

3. The implantable medical device of claim 2, wherein the insulative material surrounds the connection segment without surrounding the active segment.

4. The implantable medical device of claim 2, wherein the adhesive is disposed on the metal coating along the connection segment without being disposed on the metal coating along the active segment.

5. The implantable medical device of claim 2, wherein the connection segment is a first connection segment, and the metal substrate includes a second connection segment, the active segment disposed between the first connection segment and the second connection segment, wherein the metal coating is not on the second connection segment of the metal substrate.

6. The implantable medical device of claim 2, wherein the active segment of the metal substrate has a greater outer diameter than the connection segment of the metal substrate.

7. The implantable medical device of claim 1, wherein the electrode defines one or more apertures through a thickness thereof, and at least some of the adhesive that adheres the insulative material to the metal coating extends into at least one aperture of the one or more apertures.

8. The implantable medical device of claim 7, wherein the electrode has a hollow, cylindrical shape, and the electrode defines multiple apertures that are spaced apart from one another along a circumference of the electrode.

9. The implantable medical device of claim 1, wherein the metal substrate comprises at least one of platinum, iridium, or titanium.

10. The implantable medical device of claim 1, wherein the metal coating comprises one of titanium nitride, platinum black, or iridium oxide.

11. The implantable medical device of claim 1, wherein the metal substrate comprises a platinum alloy, and the metal coating comprises titanium nitride.

12. The implantable medical device of claim 1, wherein the insulative material comprises at least one of silicone or polyurethane.

13. The implantable medical device of claim 1, wherein the insulative material is a tubular lead body of an implantable lead of the implantable medical device.

14. The implantable medical device of claim 1, wherein the metal substrate has a hollow cylindrical shape.

15. An implantable lead comprising:

an electrode comprising a metal substrate and a metal coating, the metal substrate having a hollow cylindrical shape, the metal coating disposed on an outer surface of the metal substrate;

an adhesive disposed on the metal coating; and an insulative material secured to the electrode via the adhesive, wherein the insulative material is a tubular lead body of the implantable lead.

16. The implantable lead of claim 15, wherein the metal substrate is composed of at least one of platinum, iridium, or titanium, and the metal coating is composed of one of titanium nitride, platinum black, or iridium oxide.

17. The implantable lead of claim 15, wherein the electrode comprises a connection segment and an active segment at discrete locations along a length of the electrode, wherein the metal coating is disposed on the metal substrate along both the connection segment and the active segment.

18. The implantable lead of claim 17, wherein the insulative material surrounds the connection segment without surrounding the active segment, and the adhesive is disposed on the connection segment without being disposed on the active segment.

19. The implantable lead of claim 15, wherein the electrode defines one or more apertures through a thickness thereof, and at least some of the adhesive on the metal coating extends into at least one aperture of the one or more apertures.

20. A method of forming an implantable lead, the method comprising:

forming a metal substrate to have a hollow cylindrical shape;

applying a metal coating on an outer surface of the metal substrate;

applying an adhesive on the metal coating; and bonding an insulative material of a lead body to the metal substrate and the metal coating via the adhesive.

* * * * *